US00PP10461P

United States Patent [19]

Shaw

[11] Patent Number: Plant 10,461

[45] Date of Patent: Jun. 23, 1998

[54] STRAWBERRY PLANT NAMED 'GAVIOTA'

[75] Inventor: Douglas V. Shaw, Davis, Calif.

[73] Assignee: The Regents of the University of California, Oakland, Calif.

[21] Appl. No.: 747,507

[22] Filed: Nov. 12, 1996

[51] Int. Cl.[6] ..... A01H 5/00

[52] U.S. Cl. ..... Plt./49

[58] Field of Search ..... Plt./49, 48

[56] References Cited

U.S. PATENT DOCUMENTS

P.P. 8,660 3/1994 Voth et al. ..... Plt./49

P.P. 8,746 5/1994 Izhar et al. ..... Plt./49

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

'C205' is a new and distinct cultivar of strawberry plant of the short-day type which produces greater quantities of late-season fruit than the cultivars 'Chandler' and 'Camarosa' when grown in central California. Fruiting plants of 'C205' are smaller and more compact, more open, more erect, and less vigorous than plants of 'Chandler' or 'Camarosa'.

3 Drawing Sheets

RELATED APPLICATIONS

There are no related applications.

FIELD OF THE INVENTION

This invention relates to a new and distinctive short-day type strawberry cultivar designated as 'C205', which resulted from a cross performed in 1991 between advanced selections Cal 87.112-6 and Cal 88.270-1. The cultivar is botanically identified as *F. ×ananassa Duch.*

'C205' was first fruited at the University of California Wolfskill Experimental Orchard, near Winters, Calif. in 1992 where it was selected, originally designated Cal 91.248-2, and propagated asexually by runners. Following selecting and during testing the plant of this disclosure was designated 'CN205'. With the decision that this plant was to be released, it was given the name 'Gaviota' for the purposes of introduction into commerce and for international registration and recognition. Asexual propagules from this original source have been tested at the Watsonville Strawberry Research Facility, the South Coast Research and Extension Center, and to a limited extent in grower fields starting in 1994.

DETAILED DESCRIPTION OF THE INVENTION

Figure 1:
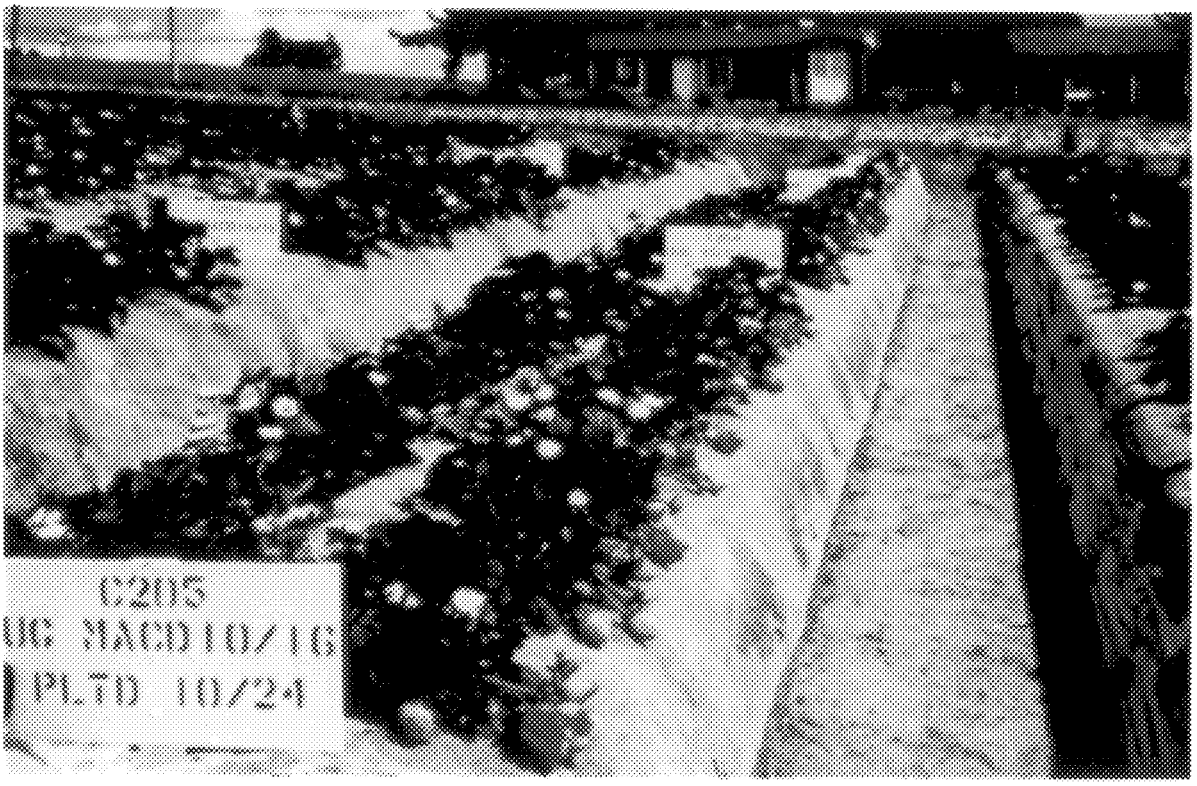
FIG. 1 depicts the general flowering and fruiting characteristics of the plant.
Figure 2:
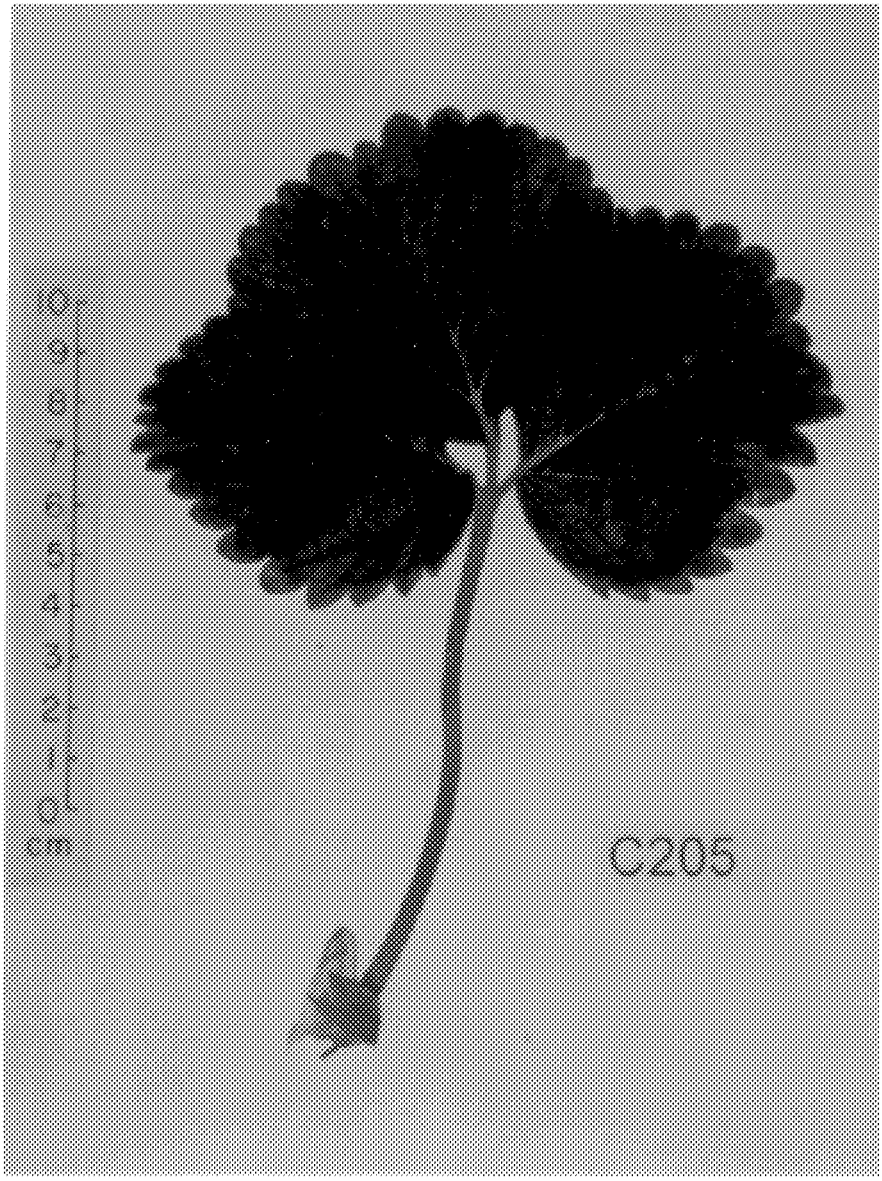
FIG. 2 depicts a typical mature leaf during late spring.
Figure 3:
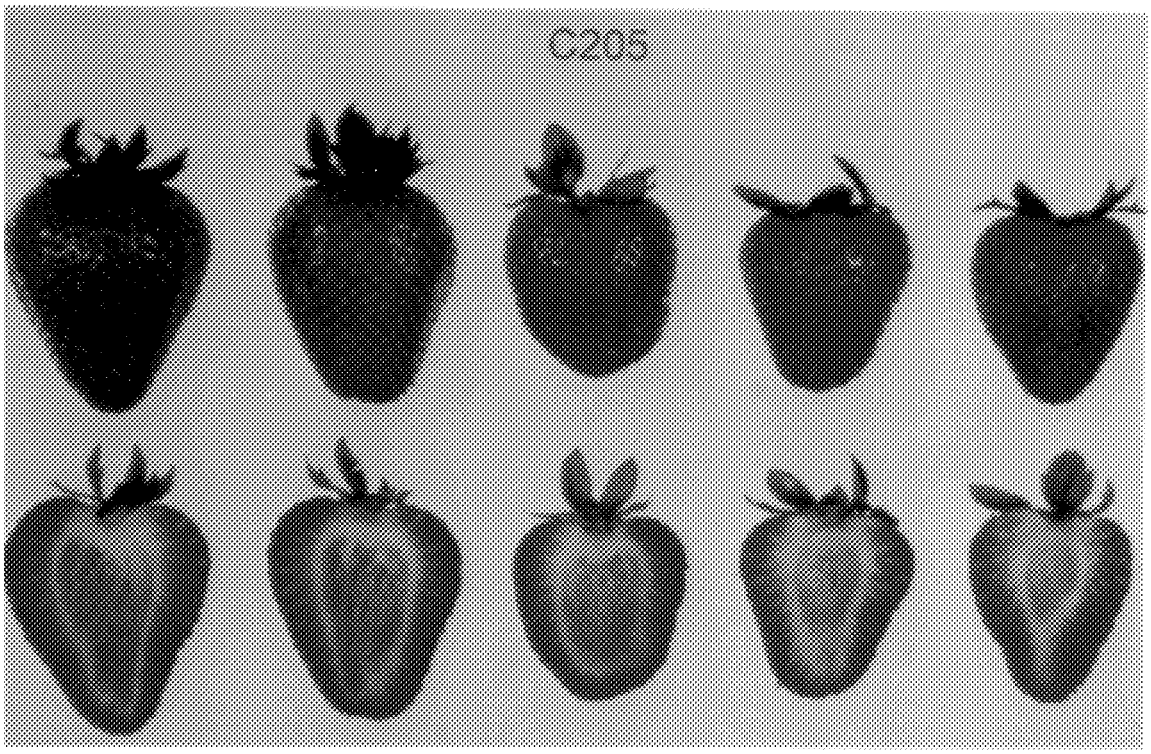
FIG. 3 depicts representative mid-season fruit.

'C205' is typical of short-day strawberry cultivars and produces fruit over an extended period when treated appropriately in arid, subtropical climates. The production pattern for 'C205' is similar to that for 'Chandler' (U.S. Plant Pat. No. 5,262) and 'Camarosa' (U.S. Plant Pat. No. 8,708), although it produces greater quantities of late-season fruit than either cultivar in central California, and is somewhat later to initiate fruiting than 'Camarosa'. 'C205' will be of special interest for winter plantings , where 'Chandler' and 'Camarosa' have been successful, and in summer plantings where 'Pajaro' (U.S. Plant Pat. No. 4,538) has been successful.

Plants and foliage: Fruiting plants of 'C205' are smaller and more compact, more open, more erect, and less vigorous than plants of 'Chandler' or 'Camarosa'. Comparative statistics for foliar characters near mid-season are given for the three cultivars in Table 1. Individual leaflets for 'C205' are larger than for 'Chandler' or 'Camarosa', and somewhat more rounded. Leaves (including petioles) are similar in length and broader than those of 'Chandler', and shorter and broader than those of 'Camarosa'. Petioles are thicker and more stiff than those of 'Chandler' and are similar to those of 'Camarosa'. Also, the upper surface of leaves for 'C205' are darker than either 'Chandler' or 'Camarosa' and the lower surfaces are somewhat lighter (Table 2). Leaves of 'C205' have variable leaf convexity, are generally more concave than leaves of 'Chandler' or 'Camarosa', and have fewer and more rounded serrations than the comparsion cultivars.

Isozymes in leaf extracts: 'C205' has been classified for three isozyme systems using starch gel electrophoresis (Table 3): Phosophoglucoisomerase (PGI), Leucine Aminopeptides (LAP), and Phosphoglucomutase (PGM). It is distinguishable from 'Chandler' but not from 'Camarosa' using this methodology. For electrophoretic procedures see: J. Amer. Soc. Hort. Sci. 106:684–687.

Disease and pest reaction: 'C205' is moderately susceptible to common leaf spot (*Ramularia tulasnei*) and Verticillium wilt (*Verticillium dahliae*), relatively resistance to powdery mildew (*sphaerotheca macolaris*) and Anthracnose crown rot (*Colletotrichum acutatum*). When treated properly, it has tolerance to two-spotted spidermites (*Tetranychus urticae*) equal or greater than 'Chandler' and 'Camarosa'. 'C205' is tolerant to strawberry viruses encountered in California.

TABLE 1

Foliar characteristics for 'C205', 'Chandler', and 'Camarosa'

| Foliar Character | Cultivar 'Chandler' | 'Camarosa' | 'C205' |
|---|---|---|---|
| Mid-tier leaflet | | | |
| Length (mm) | | | |
| mean | 64.1 | 68.7 | 71.7 |
| range | 57–69 | 60–83 | 66–85 |
| Width (mm) | | | |
| mean | 61.8 | 64.2 | 65.7 |
| range | 55–66 | 56–80 | 61–74 |
| Mid-tier leaf | | | |
| Length (mm) | | | |
| mean | 110.0 | 131.9 | 122.1 |
| range | 100–122 | 115–146 | 115–134 |
| Width (mm) | | | |
| mean | 119.5 | 121.5 | 119.2 |
| range | 109–135 | 110–147 | 108–145 |
| # Leaflets/leaf | 3 | 3 | 3 |
| Leaf convexity | most concave, some flat/convex | flat–convex, some concave | convex, few flat or concave |
| Serrations | | | |
| number | med–many | few | few to moderate |
| shape | semipointed | rounded, some semipointed | rounded to semipointed |
| Leaf pubescence | moderate | light–moderate | moderate |
| Petiole pubescence | | | |
| density | mod.–heavy | heavy | heavy |
| direction | perpendicular | perpendicular to acropetal | perpendicular |

Flowering, fruiting, fruit, and production characteristics: Comparative statistics for flower and fruit characters near mid-season are given for 'C205', 'Chandler' and 'Camarosa' in Table 4. The primary flowers for 'C205' are similar in size to 'Chandler' and 'Camarosa'; the sepals are somewhat larger than for 'Chandler' and substantially smaller than for 'Camarosa'. The calyx for 'C205' varies from slightly indented to slightly necked, and each primary flower has 4–6 petals. The fruit shape for 'C205' can vary but is typically a rounded conic, and is easily distinguished from 'Chandler' (flat conic, with some long conic) and 'Camarosa' (shortened flat conic). External and internal fruit color for 'C205' is darker than 'Chandler' and slightly darker than 'Camarosa' (Table 2). Achenes vary from yellow to dark red, and are even with the first surface or occasionally slightly extruded.

'C205' has been tested under a variety of cultural regimes, and optimal performance is obtained when nursery treatments and nutritional programs similar to those for 'Chandler' and 'Camarosa' are used. In general, 'C205' is less adapted to very early season planting but less sensitive to excess chilling than 'Camarosa'. 'C205' retains excellent fruit quality in summer planting systems.

When treated with appropriate planting regimes, 'C205' has larger fruit and produces greater yields than 'Chandler' (Table 5); 'C205' has lower yield but equal or larger sized fruit than 'Camarosa'. 'C205' is similar to 'Chandler' in its production pattern, somewhat later to initiate production than 'Camarosa', and produces substantially more late-season fruit than either comparison cultivar (with conventional winter planting in central California). Commercial appearance ratings have been comparable to or better than those for 'Chandler' and 'Camarosa'. Fruit for 'C205' is substantially firmer than fruit and 'Chandler' but slightly less firm than 'Camarosa'. Subjectively, 'C205' has very good flavor, somewhat less aromatic than 'Chandler', but with better balance and texture than 'Camarosa'. The fruit will be outstanding for both fresh market and processing, and will be useful for home garden purposes.

TABLE 2

Foliar and fruit color characteristics for 'C205', 'Chandler', and 'Camarosa'

| Color Character | Cultivar 'Chandler' | 'Camarosa' | 'C205' |
|---|---|---|---|
| Leaf color (CIELAB) | | | |
| Adaxial | | | |
| L* | | | |
| mean | 33.4 | 33.2 | 30.2 |
| range | 30.2–37.8 | 30.9–34.3 | 28.8–31.8 |
| a* | | | |
| mean | −7.5 | −7.2 | −6.3 |
| range | −6.7—8.6 | −5.6—8.9 | −5.6—7.5 |
| b* | | | |
| mean | 16.9 | 14.7 | 11.1 |
| range | 14.7–21.2 | 13.4–17.7 | 9.5–13.8 |
| Munsell | 5GY 5/6 | 2.5GY 5/5 | 2.5GY 5/5 |
| Abaxial | | | |
| L* | | | |
| mean | 48.9 | 48.7 | 49.1 |
| range | 47.1–50.0 | 47.3–50.0 | 46.9–50.3 |
| a* | | | |
| mean | −7.6 | −7.6 | −7.8 |
| range | −6.3—8.2 | −7.3—8.3 | −7.3—8.2 |
| b* | | | |
| mean | 21.1 | 20.7 | 18.6 |
| range | 18.3–23.6 | 19.8–21.8 | 16.8–20.1 |
| Munsell | 5GY 4/3 | 5GY 4/3 | 5GY 4/3 |
| Fruit color (CIELAB) | | | |
| External | | | |
| L* | | | |
| mean | 24.0 | 25.7 | 23.9 |
| range | 22.6–25.7 | 22.3–28.0 | 22.1–25.1 |
| a* | | | |
| mean | 26.9 | 22.0 | 23.9 |
| range | 23.9–29.2 | 16.7–28.0 | 21.4–25.1 |
| b* | | | |
| mean | 13.9 | 26.8 | 12.4 |
| range | 10.0–16.3 | 24.5–28.5 | 9.5–16.9 |
| Munsell | 5R 5/13 | 2.5R 4/10 | 5R 4/12 |
| Internal | | | |
| L* | | | |
| mean | 45.5 | 44.6 | 48.7 |
| range | 42.0–49.9 | 38.4–52.0 | 45.5–51.3 |
| a* | | | |
| mean | 39.0 | 39.6 | 33.1 |
| range | 32.6–43.1 | 34.3–41.5 | 30.3–36.0 |

TABLE 2-continued

Foliar and fruit color characteristics for 'C205', 'Chandler', and 'Camarosa'

| Color | Cultivar | | |
|---|---|---|---|
| Character | 'Chandler' | 'Camarosa' | 'C205' |
| b* | | | |
| mean | 29.4 | 26.7 | 24.2 |
| range | 24.7–33.8 | 24.5–28.5 | 21.2–27.2 |
| Munsell | 5R 6/11 | 7.5R 5/13 | 5R 5/13 |

*CIELAB is the abbreviation of the international color system known as "Commission Internationale De L'Eclairage" 1978. Recommendations on uniform color spaces - - - color difference equations, psychometric color terms, Supplement No. 2 to CIE Publication No. 15. PARIS.

TABLE 3

Isozyme phenotypes for 'C205', 'Chandler', and 'Camarosa'.

| | Cultivar | | |
|---|---|---|---|
| locus | 'Chandler' | 'Camarosa' | 'C205' |
| PGI | A1 | A2 | A2 |
| LAP | B3 | B3 | B3 |
| PGM | C1 | C1 | C1 |

TABLE 4

Flower and fruit characters for 'C205', 'Chandler', and 'Camarosa'

| | Cultivar | | |
|---|---|---|---|
| Character | 'Chandler' | 'Camarosa' | 'C205' |
| # petals | | | |
| mean | 5.8 | 5.5 | 5.1 |
| range | 5–7 | 5–7 | 4–6 |
| Flower position | even to | most even | exposed |

TABLE 4-continued

Flower and fruit characters for 'C205', 'Chandler', and 'Camarosa'

| | Cultivar | | |
|---|---|---|---|
| Character | 'Chandler' | 'Camarosa' | 'C205' |
| (relative to foliage) | exposed | some exposed | |
| Calyx diam. (mm) | | | |
| mean | 39.6 | 64.3 | 43.2 |
| range | 33–44 | 40–77 | 35–55 |
| Corolla diam. (mm) | | | |
| mean | 38.9 | 35.9 | 37.7 |
| range | 37–42 | 31–40 | 35–41 |
| Fruit shape | | | |
| length/width | | | |
| ratio | 1.10 | 1.15 | 1.10 |
| range | 1.00–1.43 | 0.96–1.19 | 1.08–1.12 |
| subjective | conic to flat conic | flat conic to flat | mostly rounded conic, some flat conic |
| Calyx position | slight neck | event to slight indent | even to slight indent |
| Seed position | even | even to slight indent | even |

TABLE 5

Performance of 'C205', 'Chandler', and 'Camarosa' evaluated at the Watsonville Research Facility in 1995 and 1996. All plants for these trials were harvested from Macdoel on October 17, and transplanted after one week supplemental storage. Harvest was initiated in early April and continued through the first week of September. (52" 2-row beds, 17,300 plants/acre, 100 grams/plant = 316.3 crates/acre)

| Item | Yield (g/plant) | Appearance Score | Size (g/fruit) | Firmness |
|---|---|---|---|---|
| 'Chandler' | 1,372 | 3.1 | 22.9 | 6.1 |
| 'Camarosa' | 1,820 | 3.7 | 26.3 | 7.8 |
| 'C205' | 1,443 | 3.7 | 27.4 | 7.3 |

We claim:

1. The new and distinct cultivar of strawberry plant substantially as herein described and illustrated.

* * * * *